(12) United States Patent
Akimoto et al.

(10) Patent No.: US 12,031,933 B2
(45) Date of Patent: Jul. 9, 2024

(54) SENSOR (71) Applicant: KABUSHIKI KAISHA TOSHIBA, Tokyo (JP)

(72) Inventors: Yosuke Akimoto, Yokohama Kanagawa (JP); Hiroaki Yamazaki, Yokohama Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 285 days.

(21) Appl. No.: 17/445,688

(22) Filed: Aug. 23, 2021

(65) Prior Publication Data

US 2022/0276192 A1 Sep. 1, 2022

(30) Foreign Application Priority Data

Feb. 26, 2021 (JP) .................................. 2021-029713

(51) Int. Cl.
*G01N 27/22* (2006.01)
*G01N 33/00* (2006.01)

(52) U.S. Cl.
CPC ......... *G01N 27/225* (2013.01); *G01N 27/221* (2013.01); *G01N 27/226* (2013.01); *G01N 33/0027* (2013.01)

(58) Field of Classification Search
CPC .. G01N 27/225; G01N 27/221; G01N 27/226; G01N 33/0027; G01N 27/223; G01N 2027/222

See application file for complete search history.

(56) References Cited

U.S. PATENT DOCUMENTS

| 2003/0136997 | A1* | 7/2003 | Shioga ................... H01L 27/016 257/E23.079 |
| 2009/0252278 | A1 | 10/2009 | Bashkirtsev et al. |
| 2011/0179861 | A1* | 7/2011 | Grange ................ G01N 27/225 977/773 |
| 2011/0255651 | A1 | 10/2011 | Bashkirtsev et al. |
| 2011/0259099 | A1 | 10/2011 | Hong et al. |
| 2013/0139587 | A1 | 6/2013 | Le Neel et al. |

(Continued)

FOREIGN PATENT DOCUMENTS

| CN | 1205198 A | * | 1/1999 | ........ A61F 13/15211 |
| JP | S6272354 A | * | 4/1987 | ............... A61F 5/44 |
| JP | S63-144243 A | | 6/1988 | |

(Continued)

*Primary Examiner* — Alexander Satanovsky
*Assistant Examiner* — Asm Fakhruddin
(74) *Attorney, Agent, or Firm* — Finnegan, Henderson, Farabow, Garrett & Dunner, LLP (57) ABSTRACT

According to one embodiment, a sensor includes a first sensor part. The first sensor part includes a first electrode, a first counter electrode, and a first intermediate layer located between the first electrode and the first counter electrode. The first counter electrode includes a first electrode side surface. The first electrode side surface crosses a first cross direction. The first cross direction crosses a first direction from the first electrode toward the first counter electrode. The first intermediate layer includes a first intermediate layer side surface. The first intermediate layer side surface crosses the first cross direction. The first intermediate layer side surface is recessed when referenced to the first electrode side surface.

18 Claims, 6 Drawing Sheets

(56) References Cited

U.S. PATENT DOCUMENTS

2019/0086377 A1    3/2019   Ikehashi et al.

FOREIGN PATENT DOCUMENTS

| JP | 2007-206040 A |   | 8/2007 |
|----|---------------|---|--------|
| JP | 2011-508877 A |   | 3/2011 |
| JP | 2012-508677 A |   | 4/2012 |
| JP | 2014-70945 A  |   | 4/2014 |
| JP | 2019-56607 A  |   | 4/2019 |
| KR | 101807749 B1  | * | 12/2017 |

* cited by examiner

SENSOR

CROSS-REFERENCE TO RELATED APPLICATIONS

This application is based upon and claims the benefit of priority from Japanese Patent Application No. 2021-029713, filed on Feb. 26, 2021; the entire contents of which are incorporated herein by reference.

FIELD

Embodiments described herein relate generally to a sensor.

BACKGROUND

For example, it is desirable to improve the detection performance of a sensor.

DETAILED DESCRIPTION

According to one embodiment, a sensor includes a first sensor part. The first sensor part includes a first electrode, a first counter electrode, and a first intermediate layer located between the first electrode and the first counter electrode. The first counter electrode includes a first electrode side surface. The first electrode side surface crosses a first cross direction. The first cross direction crosses a first direction from the first electrode toward the first counter electrode. The first intermediate layer includes a first intermediate layer side surface. The first intermediate layer side surface crosses the first cross direction. The first intermediate layer side surface is recessed when referenced to the first electrode side surface.

According to one embodiment, a sensor includes a first sensor part. The first sensor part includes a first electrode, a first counter electrode, and a first intermediate layer located between the first electrode and the first counter electrode. The first counter electrode includes a first non-overlap region. The first non-overlap region does not overlap the first intermediate layer in a first direction from the first electrode toward the first counter electrode.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously or illustrated in an antecedent drawing are marked with like reference numerals, and a detailed description is omitted as appropriate.

First Embodiment

Figure 1A:
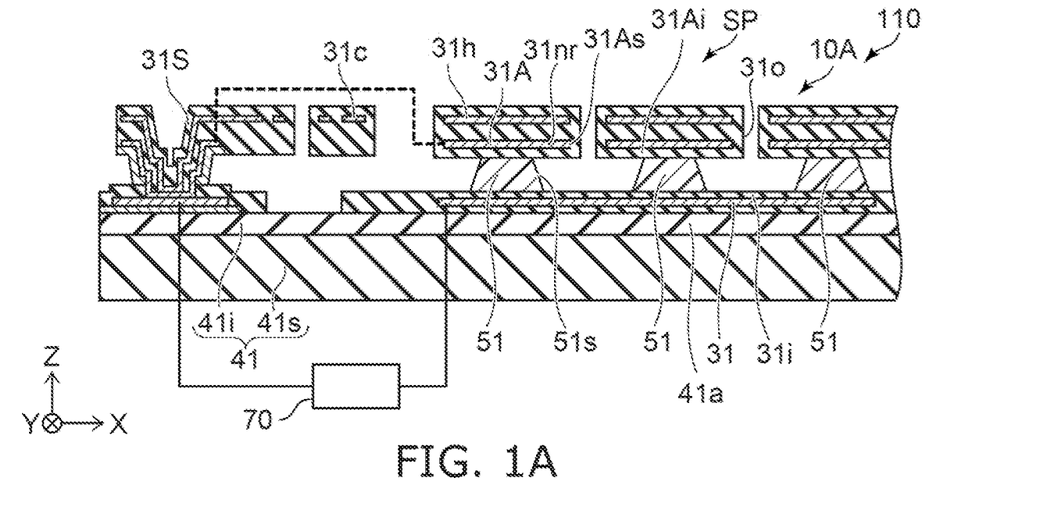
FIGS. 1A and 1B are schematic views illustrating a sensor according to a first embodiment.
Figure 1B:
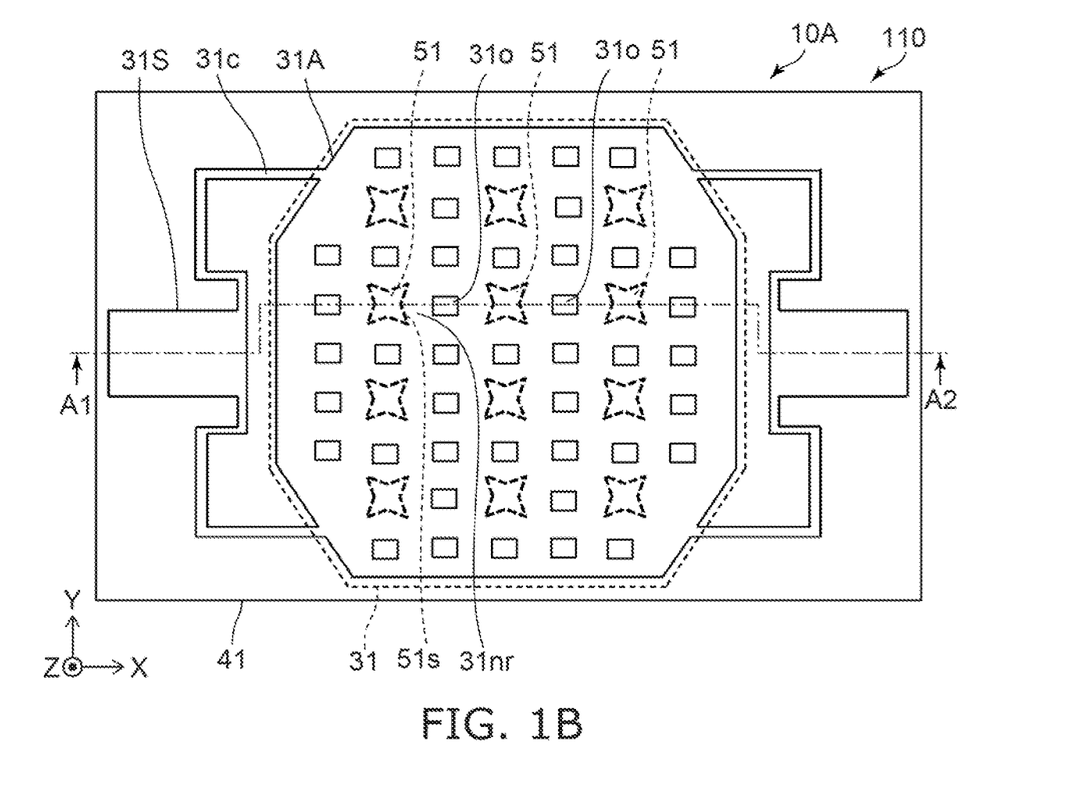

FIGS. 1A and 1B are schematic views illustrating a sensor according to a first embodiment.

FIG. 1A is a line A1-A2 cross-sectional view of FIG. 1B. FIG. 1B is a see-through plan view. Some of the portions are not illustrated in FIG. 1B for easier viewing.

As shown in FIGS. 1A and 1B, the sensor 110 according to the embodiment includes a first sensor part 10A. The first sensor part 10A includes a first electrode 31, a first counter electrode 31A, and a first intermediate layer 51. The first intermediate layer 51 is located between the first electrode 31 and the first counter electrode 31A.

In the example, the sensor 110 includes a first member 41. The first member 41 is, for example, a base body. In the example, the first member 41 includes a substrate 41s and an insulating layer 41i. The substrate 41s is, for example, a silicon substrate. The substrate 41s may include a control element such as a transistor, etc. The insulating layer 41i is located on the substrate 41s. For example, the first sensor part 10A is located on the insulating layer 41i. According to the embodiment, the first member 41 may include interconnects, etc. (not illustrated). For example, the interconnects electrically connect the first sensor part 10A and the substrate 41s. The interconnects may include contact vias.

For example, the first electrode 31 is between the first counter electrode 31A and a portion 41a of the first member 41.

A first direction from the first electrode 31 toward the first counter electrode 31A is taken as a Z-axis direction. A direction perpendicular to the Z-axis direction is taken as an X-axis direction. A direction perpendicular to the X-axis direction and the Z-axis direction is taken as a Y-axis direction. The first direction (the Z-axis direction) corresponds to the stacking direction of the first electrode 31, the first intermediate layer 51, and the first counter electrode 31A.

The first counter electrode 31A includes a first electrode side surface 31As. The first electrode side surface 31As crosses a first cross direction that crosses the first direction (the Z-axis direction) recited above. The first cross direction is, for example, one direction along the X-Y plane. The first cross direction may be, for example, the X-axis direction.

The first intermediate layer 51 includes a first intermediate layer side surface 51s. The first intermediate layer side surface 51s crosses the first cross direction recited above. The first intermediate layer side surface 51s is recessed when referenced to the first electrode side surface 31As. The first intermediate layer side surface 51s is exposed as shown in FIG. 1A. The first intermediate layer side surface 51s is exposed in a region between the first electrode 31 and the first counter electrode 31A.

As shown in FIGS. 1A and 1B, the first counter electrode 31A may include one or multiple openings 31o. The first electrode side surface 31As may be the side surface of the one or multiple openings 31o. For example, the first intermediate layer 51 does not overlap the opening 31o in the first direction (the Z-axis direction).

Multiple first intermediate layers 51 are provided in the example. The multiple first intermediate layers 51 have island shapes. The first intermediate layer side surface 51s is provided in one of the island-shaped multiple first intermediate layers 51. The first intermediate layer side surface 51s may be recessed from the opening 31o of the first counter electrode 31A.

The first electrode side surface 31As may correspond to the side surface of the outer edge of the first counter electrode 31A. The first intermediate layer side surface 51s may be recessed when referenced to the side surface of the outer edge of the first counter electrode 31A.

As shown in FIGS. 1A and 1B, for example, the first counter electrode 31A includes a first non-overlap region 31nr. The first non-overlap region 31nr does not overlap the first intermediate layer 51 in the first direction (the Z-axis direction) from the first electrode 31 toward the first counter electrode 31A.

For example, the first electrode 31 and the first counter electrode 31A may be electrically connected with a circuit part 70. For example, the first counter electrode 31A may be electrically connected with the circuit part 70 via a conductive member that is located in a connection supporter 31S. The circuit part 70 is configured to detect the electrical capacitance between the first electrode 31 and the first counter electrode 31A.

For example, the first electrical capacitance between the first electrode 31 and the first counter electrode 31A changes according to the change of the humidity in a space SP at the periphery of the first sensor part 10A.

For example, water (a gas that includes water) that exists in the space SP at the periphery of the first sensor part 10A reaches the first intermediate layer side surface 51s of the first intermediate layer 51 by passing through the opening 31o, passing by the outer edge of the first counter electrode 31A, etc. For example, the water (the gas that includes water) adheres to the first intermediate layer side surface 51s. At least a portion of the water may be incorporated into the first intermediate layer 51. The water that is adhered to or incorporated into the first intermediate layer 51 causes the relative dielectric constant of the first intermediate layer 51 to change. The electrical capacitance changes according to the change of the relative dielectric constant.

The humidity in the space SP can be detected by detecting the change of the electrical capacitance. The sensor 110 is, for example, a capacitance change humidity sensor.

According to the embodiment, the first intermediate layer side surface 51s of the first intermediate layer 51 is exposed. Therefore, the surface area that can adsorb water is wide. For example, the ratio of the surface area of the first intermediate layer side surface 51s to the surface area of the sensor 110 is high. For example, the ratio of the surface area of the portion of the first intermediate layer 51 that is exposed to the outside to the volume of the first intermediate layer 51 is high. Thereby, the electrical capacitance between the first electrode 31 and the first counter electrode 31A changes with high sensitivity to the change of the humidity. For example, the change of the humidity can be detected with high sensitivity. For example, the change of the humidity can be detected at a high response rate. According to the embodiment, the detection performance can be improved.

For example, a reference example may be considered in which a first intermediate layer 51 that is a continuous film is located between the first electrode 31 and the first counter electrode 31A that includes the opening 31o illustrated in FIG. 1A. In the reference example, the upper surface of a portion of the first intermediate layer 51 is exposed in the opening 31o. The water adheres to the upper surface of the exposed portion of the first intermediate layer 51. This portion to which the water adheres does not exist between the first electrode 31 and the first counter electrode 31A. Therefore, it is difficult for the water to contribute to the change of the electrical capacitance. For example, in the reference example, the water can penetrate the interior of the first intermediate layer 51 and exist in the region between the first electrode 31 and the first counter electrode 31A after sufficient time has elapsed after the adhesion of the water. In such a case, the electrical capacitance is changed by the water (the gas that includes water). However, a long period of time is necessary for the water to reach the region between the first electrode 31 and the first counter electrode 31A. Therefore, in the reference example, the response time is long.

Conversely, according to the embodiment, the humidity can be detected with high sensitivity. The humidity can be detected at a high response rate.

The first intermediate layer 51 may contact the first electrode 31 and the first counter electrode 31A. As shown in FIG. 1A, a first insulating film 31i may be located around the first electrode 31. The first intermediate layer 51 may contact the first insulating film 31i. A first counter insulating film 31Ai may be located around the first counter electrode 31A. The first intermediate layer 51 may contact the first counter insulating film 31Ai. The first insulating film 31i and the first counter insulating film 31Ai includes, for example, silicon and nitrogen. The electrodes are protected by these insulating films.

A gap may not be provided between the first electrode 31 and the first intermediate layer 51. A gap may not be provided between the first counter electrode 31A and the first intermediate layer 51. By not providing a gap, for example, the change of the distance between the first electrode 31 and the first counter electrode 31A can be suppressed. The change of the electrical capacitance caused by factors other than the humidity can be suppressed thereby. A highly-accurate detection is possible.

As shown in FIG. 1A, the first sensor part 10A may include a first conductive member 31h. The first counter electrode 31A is located between the first intermediate layer 51 and the first conductive member 31h. The temperature of the first conductive member 31h may be increased by supplying a current to the first conductive member 31h. The first conductive member 31h is, for example, a heater. The first conductive member 31h may be electrically connected with an external circuit (e.g., the circuit part 70) via a connection portion 31c. The connection portion 31c may be omitted.

In one example, the first electrode 31 and the first counter electrode 31A include, for example, a metal. At least one of the first electrode 31 or the first counter electrode 31A include, for example, at least one selected from the group consisting of Al, Cu, and Ti. At least one of the first electrode 31 or the first counter electrode 31A may include, for example, TiN. At least one of the first electrode 31 or the first counter electrode 31A may include, for example, Si. The hygroscopicity of these materials may be low.

According to the embodiment, for example, the hygroscopicity of the first intermediate layer 51 is greater than the hygroscopicity of the first electrode 31 and greater than the hygroscopicity of the first counter electrode 31A. For example, the first intermediate layer 51 includes a resin. For example, the first intermediate layer 51 may include polyimide. For example, the hygroscopicity of the resin is greater than the hygroscopicity of the materials described above that are used as the electrodes. The change of the humidity can be detected at a high response rate. The change of the humidity can be detected with high accuracy.

The first intermediate layer 51 may include an oxide. For example, the first intermediate layer 51 may include silicon and oxygen. High hygroscopicity is easily obtained by using an oxide. The first intermediate layer 51 may include silicon oxide. The first intermediate layer 51 may be porous. A high hygroscopicity is easily obtained.

Figure 2:
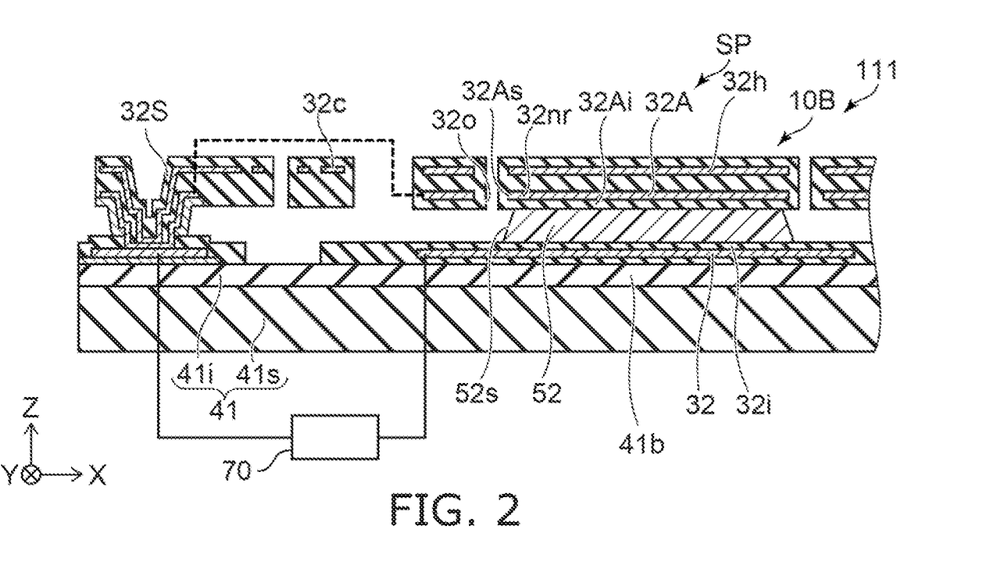
FIG. 2 is a schematic cross-sectional view illustrating a sensor according to the first embodiment.

FIG. 2 is a schematic cross-sectional view illustrating a sensor according to the first embodiment.

As shown in FIG. 2, the sensor 111 according to the embodiment includes a second sensor part 10B. The sensor 111 may further include the first sensor part 10A illustrated in FIG. 1A, etc.

The second sensor part 10B includes a second electrode 32, a second counter electrode 32A, and a second intermediate layer 52. The second intermediate layer 52 is located between the second electrode 32 and the second counter electrode 32A. The second counter electrode 32A includes a second electrode side surface 32As. The second electrode side surface 32As crosses a second cross direction that crosses a second direction from the second electrode 32 toward the second counter electrode 32A. The second direction may be substantially parallel to the first direction. The second direction may be, for example, the Z-axis direction. The second cross direction may be, for example, one direction along the X-Y plane. The second cross direction is, for example, the X-axis direction.

The second intermediate layer 52 includes a second intermediate layer side surface 52s. The second intermediate layer side surface 52s crosses the second cross direction. The second intermediate layer side surface 52s is recessed when referenced to the second electrode side surface 32As. The second intermediate layer side surface 52s is exposed in the region between the second electrode 32 and the second counter electrode 32A. For example, the second counter electrode 32A includes a second non-overlap region 32nr. The second non-overlap region 32nr does not overlap the second intermediate layer 52 in the second direction (e.g., the Z-axis direction).

For example, the second electrode 32 and the second counter electrode 32A may be electrically connected with the circuit part 70. For example, the second counter electrode 32A may be electrically connected with the circuit part 70 via a conductive member that is located in a connection supporter 32S. The circuit part 70 is configured to detect the electrical capacitance between the second electrode 32 and the second counter electrode 32A.

A first surface area of the first intermediate layer 51 in a first plane (the X-Y plane) that crosses the first direction (the Z-axis direction) is different from a second surface area of the second intermediate layer 52 in a second plane (the X-Y plane) that crosses the second direction (the Z-axis direction).

By setting different surface areas, the change of the electrical capacitance with respect to the change of the humidity has different characteristics between the first sensor part 10A and the second sensor part 10B. For example, different response rates are obtained. According to the second embodiment as well, a sensor can be provided in which the detection performance can be improved.

In the sensor 111, the first sensor part 10A and the second sensor part 10B may be located at one first member 41. For example, as shown in FIG. 1A, the first electrode 31 is between the first counter electrode 31A and the portion 41a of the first member 41. As shown in FIG. 2, the second electrode 32 is between the second counter electrode 32A and another portion 41b of the first member 41.

In the sensor 111, the second electrode 32 may be continuous with the first electrode 31. The second electrode 32 may be discontinuous with the first electrode 31.

In the sensor 111, a second insulating film 32i may be located around the second electrode 32. The second intermediate layer 52 may contact the second insulating film 32i. A second counter insulating film 32Ai may be located around the second counter electrode 32A. The second intermediate layer 52 may contact the second counter insulating film 32Ai. The second insulating film 32i and the second counter insulating film 32Ai include, for example, silicon and nitrogen. The electrodes are protected by these insulating films.

The second sensor part 10B may include a second conductive member 32h. The second counter electrode 32A is located between the second intermediate layer 52 and the second conductive member 32h. The temperature of the second conductive member 32h may be increased by supplying a current to the second conductive member 32h. The second conductive member 32h is, for example, a heater. The second conductive member 32h may be electrically connected with an external circuit (e.g., the circuit part 70) via a connection portion 32c. The connection portion 32c may be omitted.

Figure 3A:
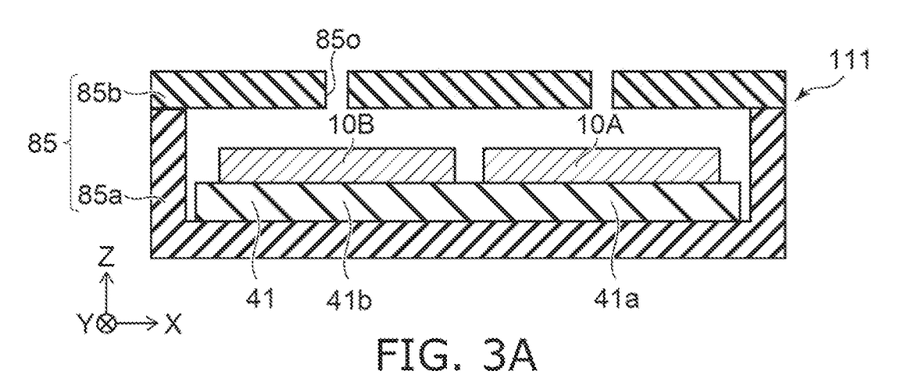
FIGS. 3A and 3B are schematic views illustrating a sensor according to the first embodiment.
Figure 3B:
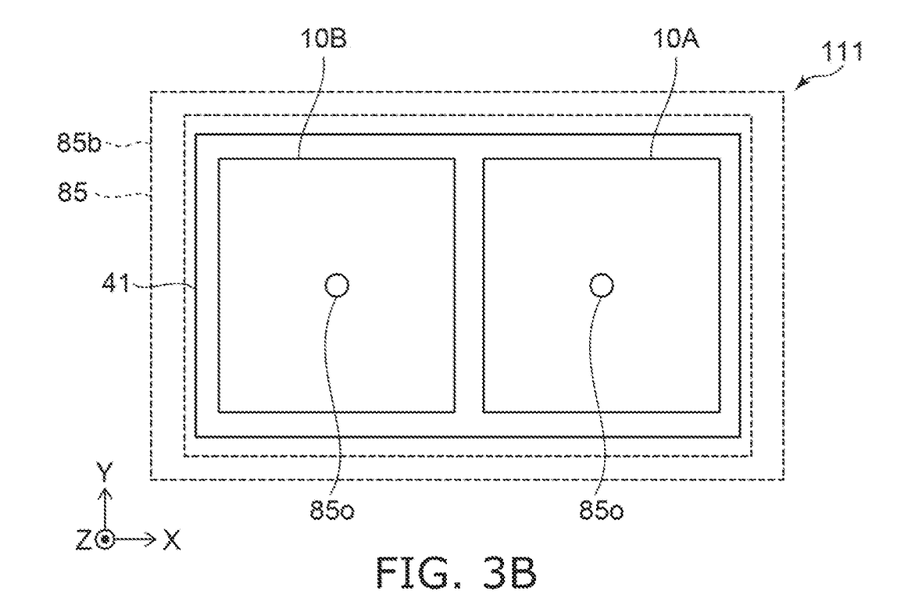

FIGS. 3A and 3B are schematic views illustrating a sensor according to the first embodiment.

FIG. 3A is a cross-sectional view. FIG. 3B is a see-through plan view.

As shown in FIGS. 3A and 3B, the sensor 111 may include a housing 85. The housing 85 includes a lid part 85b. In the example, the housing 85 includes a base 85a. The first sensor part 10A and the second sensor part 10B are located between the base 85a and the lid part 85b. The base 85a and the lid part 85b may be connected.

The lid part 85b includes a lid opening 85o. The lid opening 85o overlaps the first sensor part 10A in the first direction (the Z-axis direction). Another lid opening 85o overlaps the second sensor part 10B in the second direction (the Z-axis direction). The water (the gas that includes water) in the external atmosphere reaches the first sensor part 10A and the second sensor part 10B via the lid opening 85o. In the sensor 111, the base 85a may be omitted, and the first member 41 may perform the function of the base 85a.

Figure 4:
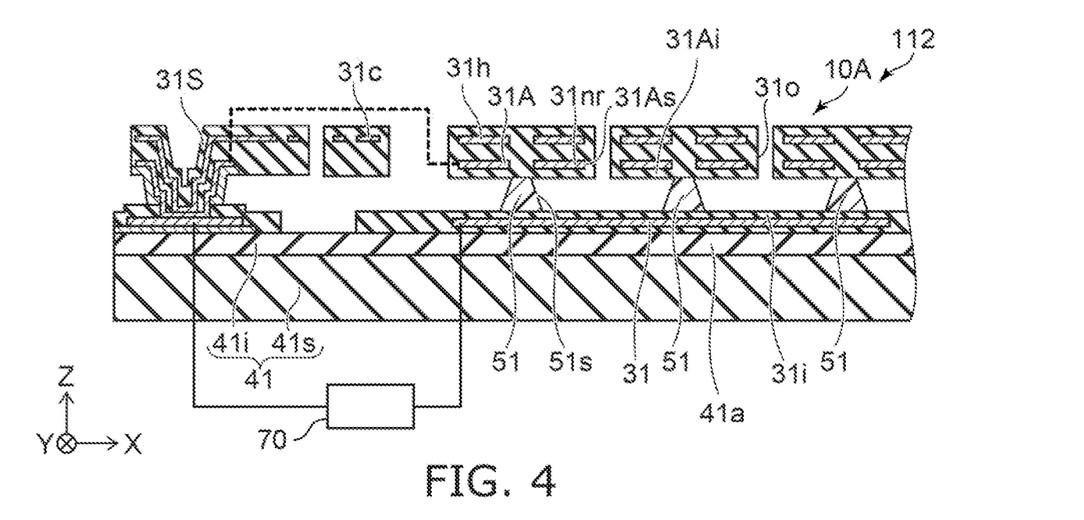
FIG. 4 is a schematic cross-sectional view illustrating a sensor according to the first embodiment.

FIG. 4 is a schematic cross-sectional view illustrating a sensor according to the first embodiment.

As shown in FIG. 4, the sensor 112 according to the embodiment includes the first sensor part 10A. In the first sensor part 10A of the example, at least a portion of the first intermediate layer 51 does not overlap the first counter electrode 31A in the first direction (the Z-axis direction). For example, the first intermediate layer 51 may be visible via the first counter insulating film 31Ai. An inspection of the first intermediate layer 51 is easier.

Second Embodiment

Figure 5:
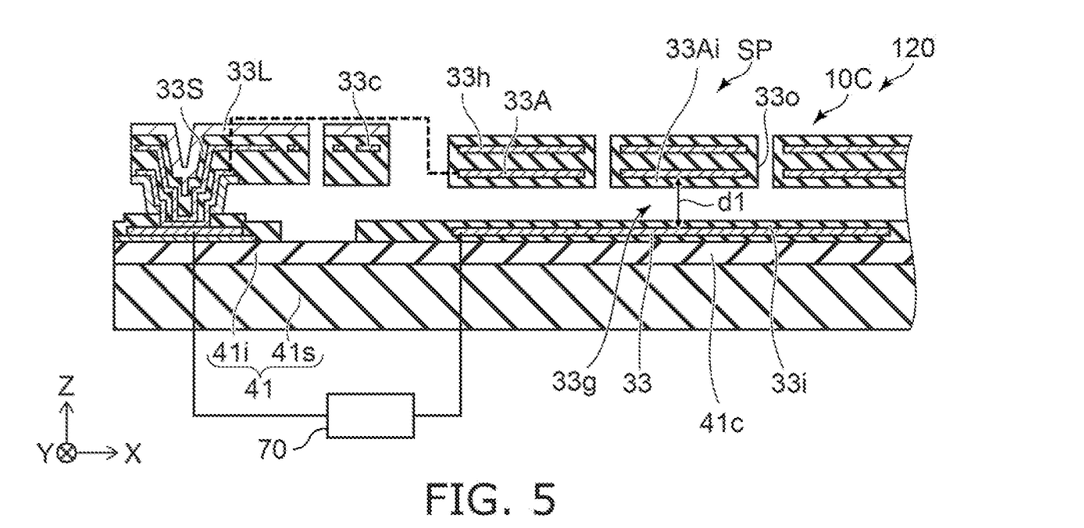
FIG. 5 is a schematic cross-sectional view illustrating a sensor according to a second embodiment.

FIG. 5 is a schematic cross-sectional view illustrating a sensor according to a second embodiment.

As shown in FIG. 5, the sensor 120 according to the embodiment includes a third sensor part 10C. The sensor 120 may further include the first sensor part 10A illustrated in FIG. 1A, etc. The sensor 120 may include the first member 41.

The third sensor part 10C includes a third electrode 33 and a third counter electrode 33A. The third electrode 33 is fixed to another portion 41c of the first member 41. The third electrode 33 is between the third counter electrode 33A and the other portion 41c of the first member 41 in a third direction (e.g., the Z-axis direction) from the third electrode 33 toward the third counter electrode 33A. A gap 33g is located between the third electrode 33 and the third counter electrode 33A. For example, the third counter electrode 33A is supported by a connection supporter 33S via a connection portion 33c.

For example, the third electrode 33 and the third counter electrode 33A may be electrically connected with the circuit part 70. For example, the third counter electrode 33A may be electrically connected with the circuit part 70 via a conductive member that is located in the connection supporter 33S. The circuit part 70 is configured to detect the electrical capacitance between the third electrode 33 and the third counter electrode 33A.

The electrical capacitance between the third electrode 33 and the third counter electrode 33A changes according to the concentration of a first element in the space SP at the periphery of the third sensor part 10C. The first element is, for example, hydrogen, etc. For example, a distance d1 between the third electrode 33 and the third counter electrode 33A changes according to the concentration of the first element. For example, the first element such as hydrogen, etc., adheres to the portion (e.g., the connection portion 33c) that supports the third counter electrode 33A. The first element such as hydrogen, etc., may be stored in the portion (e.g., the connection portion 33c) that supports the third counter electrode 33A. The portion (e.g., the connection portion 33c) that supports the third counter electrode 33A is deformed thereby. The distance d1 between the third electrode 33 and the third counter electrode 33A changes due to the deformation according to the concentration of the first element.

The concentration of the first element (e.g., hydrogen, etc.) can be detected by detecting the change of the electrical capacitance that accompanies the change of the distance d1. The third sensor part 10C is, for example, a capacitive gas sensor.

For example, the portion (e.g., the connection portion 33c) that supports the third counter electrode 33A may include a first layer 33L. The first layer 33L includes, for example, Pd, Cu, and Si. In such a case, the first layer 33L easily stores hydrogen which is an example of the first element. Hydrogen can be detected with high sensitivity.

The third sensor part 10C may include a third conductive member 33h. The third counter electrode 33A is located between the third electrode 33 and the third conductive member 33h. The temperature of the third conductive member 33h may be increased by supplying a current to the third conductive member 33h. The third conductive member 33h is, for example, a heater. The third conductive member 33h may be electrically connected with an external circuit (e.g., the circuit part 70) via the connection portion 33c.

In the sensor 120, a third insulating film 33i may be located around the third electrode 33. A third counter insulating film 33Ai may be located around the third counter electrode 33A. The third insulating film 33i and the third counter insulating film 33Ai include, for example, silicon and nitrogen. The electrodes are protected by these insulating films.

For example, as described with reference to FIG. 1A, the first electrode 31 is between the first counter electrode 31A and the portion 41a of the first member 41 in the first direction (the Z-axis direction). As shown in FIG. 5, the third electrode 33 is fixed to the other portion 41c of the first member 41. The first sensor part 10A and the third sensor part 10C are located at one first member 41. For example, the humidity and the hydrogen concentration can be detected. A small sensor can be provided.

For example, the sacrificial layer that is used when forming the third sensor part 10C may be used as the first intermediate layer 51 of the first sensor part 10A. For example, the third sensor part 10C is obtained by removing the sacrificial layer. The first intermediate layer 51 of the first sensor part 10A is obtained by causing a portion of the sacrificial layer to remain. The sensor that includes the first and third sensor parts 10A and 10C can be manufactured with high productivity.

Figure 6A:
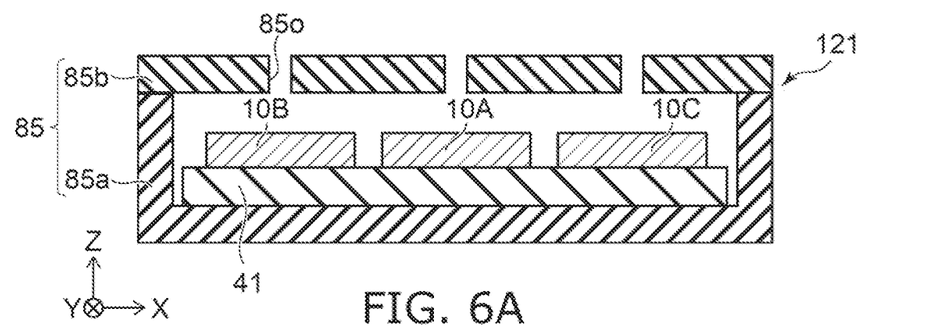
FIGS. 6A and 6B are schematic views illustrating a sensor according to the second embodiment.
Figure 6B:
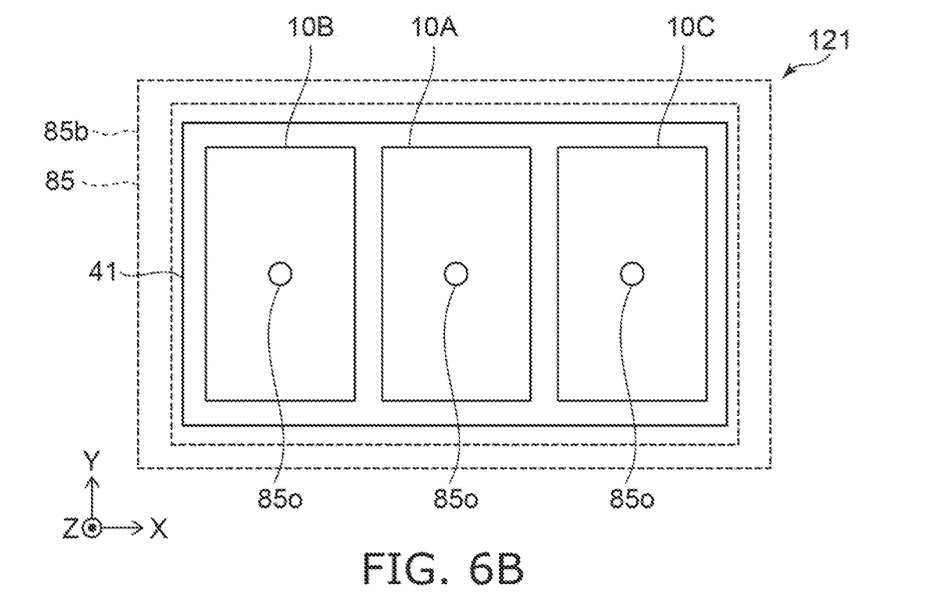

FIGS. 6A and 6B are schematic views illustrating a sensor according to the second embodiment.

FIG. 6A is a cross-sectional view. FIG. 68 is a see-through plan view.

As shown in FIGS. 6A and 6B, the sensor 121 according to the embodiment includes the first sensor part 10A, the second sensor part 10B, and the third sensor part 10C. The first sensor part 10A and the second sensor part 10B are, for example, humidity sensors. The surface area of the intermediate layer is different between the first sensor part 10A and the second sensor part 10B. The third sensor part 10C is a gas sensor (e.g., a hydrogen sensor).

In the example, the sensor 121 includes the housing 85. The housing 85 includes the lid part 85b. In the example, the housing 85 includes the base 85a. The first sensor part 10A, the second sensor part 10B, and the third sensor part 10C are located between the base 85a and the lid part 85b. The base 85a and the lid part 85b may be connected.

Multiple lid openings 85o are provided in the lid part 85b. One of the multiple lid openings 85o overlaps the first sensor part 10A in the first direction (the Z-axis direction). Another one of the multiple lid openings 85o overlaps the second sensor part 10B in the second direction (the Z-axis direction). Another one of the multiple lid openings 85o overlaps the third sensor part 10C in the third direction (the Z-axis direction).

The water (the gas that includes water) in the external atmosphere reaches the first sensor part 10A and the second sensor part 10B via the lid opening 85o. The first element (e.g., hydrogen, etc.) in the external atmosphere reaches the third sensor part 10C via the lid opening 85o. In the sensor 121, the base 85a may be omitted, and the first member 41 may perform the function of the base 85a.

Figure 7A:
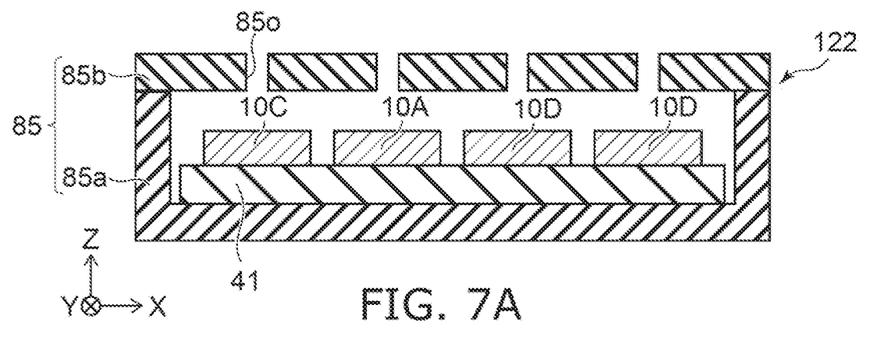
FIGS. 7A and 7B are schematic views illustrating a sensor according to the second embodiment.
Figure 7B:
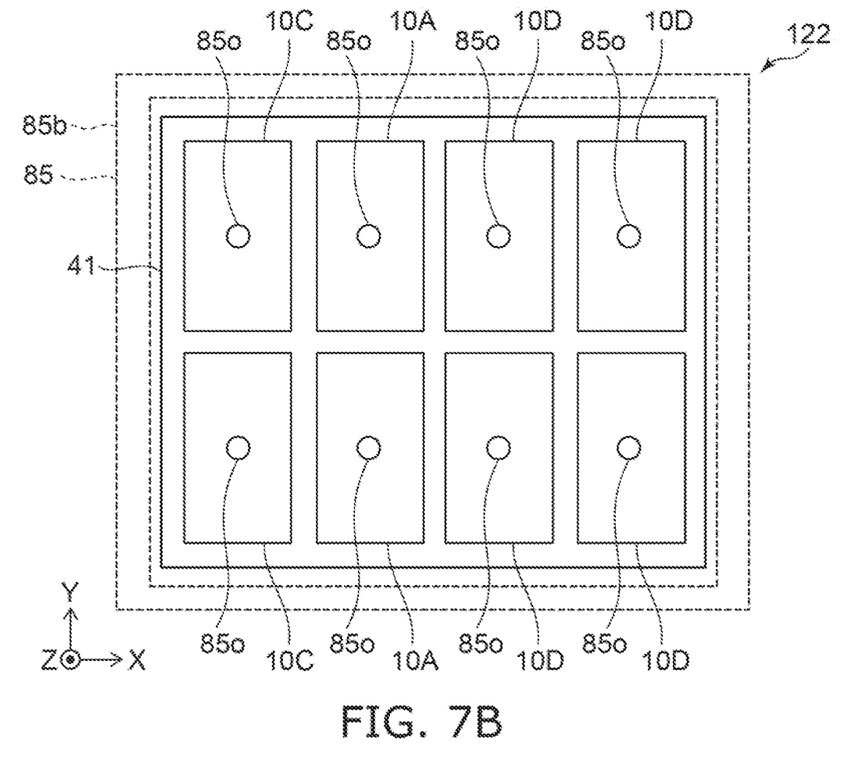

FIGS. 7A and 7B are schematic views illustrating a sensor according to the second embodiment.

FIG. 7A is a cross-sectional view. FIG. 7B is a see-through plan view.

As shown in FIGS. 7A and 7B, the sensor 122 according to the embodiment includes the first sensor part 10A, the third sensor part 10C, and a fourth sensor part 10D. The first sensor part 10A is, for example, a humidity sensor. The third sensor part 10C is a capacitive gas sensor (e.g., a hydrogen sensor). The fourth sensor part 10D is a thermal conduction gas sensor. Multiple first sensor parts 10A may be provided. Multiple third sensor parts 10C may be provided. Multiple fourth sensor parts 10D may be provided.

For example, the position of one of the multiple lid openings 85o matches the position of one of the multiple sensor parts in the Z-axis direction.

Embodiments may include the following configurations (e.g., technological proposals).

Configuration 1
A sensor, comprising:
a first sensor part,
the first sensor part including
a first electrode,
a first counter electrode, and
a first intermediate layer located between the first electrode and the first counter electrode,
the first counter electrode including a first electrode side surface,
the first electrode side surface crossing a first cross direction,
the first cross direction crossing a first direction from the first electrode toward the first counter electrode,
the first intermediate layer including a first intermediate layer side surface,
the first intermediate layer side surface crossing the first cross direction,
the first intermediate layer side surface being recessed when referenced to the first electrode side surface.

Configuration 2
The sensor according to Configuration 1, wherein
the first intermediate layer side surface is exposed.

Configuration 3
A sensor, comprising:
a first sensor part,
the first sensor part including
a first electrode,
a first counter electrode, and
a first intermediate layer located between the first electrode and the first counter electrode,
the first counter electrode including a first non-overlap region,
the first non-overlap region not overlapping the first intermediate layer in a first direction from the first electrode toward the first counter electrode.

Configuration 4
The sensor according to any one of Configurations 1 to 3, wherein
at least a portion of the first intermediate layer does not overlap the first counter electrode in the first direction.

Configuration 5
The sensor according to any one of Configurations 1 to 4, wherein
the first intermediate layer contacts the first electrode and the first counter electrode.

Configuration 6
The sensor according to any one of Configurations 1 to 5, wherein
a first electrical capacitance between the first electrode and the first counter electrode changes according to a change of a humidity in a space at a periphery of the first sensor part.

Configuration 7
The sensor according to any one of Configurations 1 to 6, wherein
a hygroscopicity of the first intermediate layer is greater than a hygroscopicity of the first electrode and greater than a hygroscopicity of the first counter electrode.

Configuration 8
The sensor according to any one of Configurations 1 to 7, wherein
the first intermediate layer includes a resin.

Configuration 9
The sensor according to any one of Configurations 1 to 8, wherein
the first intermediate layer includes polyimide.

Configuration 10
The sensor according to any one of Configurations 1 to 9, wherein
the first intermediate layer includes an oxide.

Configuration 11
The sensor according to any one of Configurations 1 to 7, wherein the first intermediate layer includes silicon and oxygen.

Configuration 12
The sensor according to any one of Configurations 1 to 11, wherein
the first intermediate layer is porous.

Configuration 13
The sensor according to any one of Configurations 1 to 12, wherein
the first counter electrode includes one or a plurality of openings, and
the first electrode side surface is a side surface of the one or a plurality of openings.

Configuration 14
The sensor according to Configuration 13, wherein
the first intermediate layer does not overlap the opening in the first direction.

Configuration 15
The sensor according to any one of Configurations 1 to 14, further comprising:
a second sensor part,
the second sensor part including
a second electrode,
a second counter electrode, and
a second intermediate layer located between the second electrode and the second counter electrode,
the second counter electrode including a second electrode side surface,
the second electrode side surface crossing a second cross direction,
the second cross direction crossing a second direction,
the second direction being from the second electrode toward the second counter electrode,
the second intermediate layer including a second intermediate layer side surface,
the second intermediate layer side surface crossing the second cross direction,
the second intermediate layer side surface being recessed when referenced to the second electrode side surface,
a first surface area of the first intermediate layer in a first plane crossing the first direction is different from a second surface area of the second intermediate layer in a second plane crossing the second direction.

Configuration 16
The sensor according to any one of Configurations 1 to 14, further comprising:
a second sensor part,
the second sensor part including
a second electrode,
a second counter electrode,
a second intermediate layer located between the second electrode and the second counter electrode,
the second counter electrode including a second non-overlap region,
the second non-overlap region not overlapping the second intermediate layer in a second direction from the second electrode toward the second counter electrode, a first surface area of the first intermediate layer in a first plane being different from a second surface area of the second intermediate layer in a second plane,
the first plane crossing the first direction,
the second plane crossing the second direction.

Configuration 17

The sensor according to Configuration 15 or 16, further comprising:
a first member,
the first electrode being between the first counter electrode and a portion of the first member,
the second electrode being between the second counter electrode and an other portion of the first member,
the second electrode being continuous with the first electrode.

Configuration 18

The sensor according to any one of Configurations 1 to 16, further comprising:
a first member; and
a third sensor part,
the first electrode being between the first counter electrode and a portion of the first member in the first direction,
the third sensor part including a third electrode and a third counter electrode,
the third electrode being fixed to an other portion of the first member,
the third electrode being between the third counter electrode and the other portion of the first member in a third direction,
the third direction being from the third electrode toward the third counter electrode,
a gap being located between the third electrode and the third counter electrode,
an electrical capacitance between the third electrode and the third counter electrode changing according to a concentration of a first element in a space at a periphery of the third sensor part.

Configuration 19

The sensor according to Configuration 18, wherein
a distance between the third electrode and the third counter electrode changes according to the concentration of the first element.

Configuration 20

The sensor according to any one of Configurations 1 to 19, further comprising:
a housing,
the housing including a lid part,
the lid part including a lid opening,
the lid opening overlapping the first sensor part in the first direction.

According to embodiments, a sensor can be provided in which the detection performance can be improved.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in sensors such as electrodes, intermediate layers, members, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all sensors practicable by an appropriate design modification by one skilled in the art based on the sensors described above as embodiments of the invention also are within the scope of the invention to the extent that the spirit of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A sensor, comprising:
a first sensor part, the first sensor part including
a first electrode,
a first counter electrode, and
a first intermediate layer located between the first electrode and the first counter electrode;
a first member; and
a third sensor part,
the first counter electrode including a first electrode side surface,
the first electrode side surface crossing a first cross direction,
the first cross direction crossing a first direction from the first electrode toward the first counter electrode,
the first intermediate layer including a first intermediate layer side surface,
the first intermediate layer side surface crossing the first cross direction,
the first intermediate layer side surface being recessed when referenced to the first electrode side surface,
at least a part of the first intermediate layer side surface being inclined with respect to the first direction,
the first electrode being between the first counter electrode and a portion of the first member in the first direction,
the third sensor part including a third electrode and a third counter electrode,
the third electrode being fixed to an other portion of the first member,
the third electrode being between the third counter electrode and the other portion of the first member in a third direction,
the third direction being from the third electrode toward the third counter electrode,
a gap being located between the third electrode and the third counter electrode,
an electrical capacitance between the third electrode and the third counter electrode changing according to a concentration of a first element in a space at a periphery of the third sensor part.

2. The sensor according to claim 1, wherein
the first intermediate layer side surface is exposed.

3. The sensor according to claim 1, wherein
at least a portion of the first intermediate layer does not overlap the first counter electrode in the first direction.

4. The sensor according to claim 1, wherein
the first intermediate layer contacts the first electrode and the first counter electrode.

5. The sensor according to claim 1, wherein
a first electrical capacitance between the first electrode and the first counter electrode changes according to a change of a humidity in a space at a periphery of the first sensor part.

6. The sensor according to claim 1, wherein
a hygroscopicity of the first intermediate layer is greater than a hygroscopicity of the first electrode and greater than a hygroscopicity of the first counter electrode.

7. The sensor according to claim 1, wherein
the first intermediate layer includes a resin.

8. The sensor according to claim 1, wherein
the first intermediate layer includes polyimide.

9. The sensor according to claim 1, wherein
the first intermediate layer includes an oxide.

10. The sensor according to claim 1, wherein the first intermediate layer includes silicon and oxygen.

11. The sensor according to claim 1, wherein
the first intermediate layer is porous.

12. The sensor according to claim 1, wherein
the first counter electrode includes one or a plurality of openings, and
the first electrode side surface is a side surface of the one or a plurality of openings.

13. The sensor according to claim 12, wherein
the first intermediate layer does not overlap the opening in the first direction.

14. A sensor, comprising:
a first sensor part; and
a second sensor part,
the first sensor part including
a first electrode,
a first counter electrode, and
a first intermediate layer located between the first electrode and the first counter electrode,
the first counter electrode including a first electrode side surface,
the first electrode side surface crossing a first cross direction,
the first cross direction crossing a first direction from the first electrode toward the first counter electrode,
the first intermediate layer including a first intermediate layer side surface,
the first intermediate layer side surface crossing the first cross direction,
the first intermediate layer side surface being recessed when referenced to the first electrode side surface,
the second sensor part including
a second electrode,
a second counter electrode, and
a second intermediate layer located between the second electrode and the second counter electrode,
the second counter electrode including a second electrode side surface,
the second electrode side surface crossing a second cross direction,
the second cross direction crossing a second direction,
the second direction being from the second electrode toward the second counter electrode,
the second intermediate layer including a second intermediate layer side surface,
the second intermediate layer side surface crossing the second cross direction,
the second intermediate layer side surface being recessed when referenced to the second electrode side surface,
a first surface area of the first intermediate layer in a first plane crossing the first direction is different from a second surface area of the second intermediate layer in a second plane crossing the second direction.

15. A sensor, comprising:
a first sensor part; and
a second sensor part,
the first sensor part including
a first electrode,
a first counter electrode, and
a first intermediate layer located between the first electrode and the first counter electrode,
the first counter electrode including a first electrode side surface,
the first electrode side surface crossing a first cross direction,
the first cross direction crossing a first direction from the first electrode toward the first counter electrode,
the first intermediate layer including a first intermediate layer side surface,
the first intermediate layer side surface crossing the first cross direction,
the first intermediate layer side surface being recessed when referenced to the first electrode side surface,
the second sensor part including
a second electrode,
a second counter electrode,
a second intermediate layer located between the second electrode and the second counter electrode,
the second counter electrode including a second non-overlap region,
the second non-overlap region not overlapping the second intermediate layer in a second direction from the second electrode toward the second counter electrode,
a first surface area of the first intermediate layer in a first plane being different from a second surface area of the second intermediate layer in a second plane,
the first plane crossing the first direction,
the second plane crossing the second direction.

16. The sensor according to claim 14, further comprising:
a first member,
the first electrode being between the first counter electrode and a portion of the first member,
the second electrode being between the second counter electrode and an other portion of the first member,
the second electrode being continuous with the first electrode.

17. The sensor according to claim 1, wherein
a distance between the third electrode and the third counter electrode changes according to the concentration of the first element.

18. The sensor according to claim 1, further comprising:
a housing,
the housing including a lid part,
the lid part including a lid opening,
the lid opening overlapping the first sensor part in the first direction.

* * * * *